US010739324B2

(12) United States Patent
Bahrami

(10) Patent No.: US 10,739,324 B2
(45) Date of Patent: Aug. 11, 2020

(54) HIGHLY SELECTIVE NOX SENSOR IN THE PRESENCE OF NH3

(71) Applicant: Cummins Emission Solutions, Inc., Columbus, IN (US)

(72) Inventor: Behnam Bahrami, Indianapolis, IN (US)

(73) Assignee: Cummins Emission Solutions, Inc., Columbus, IN (US)

(*) Notice: Subject to any disclaimer, the term of this patent is extended or adjusted under 35 U.S.C. 154(b) by 0 days.

(21) Appl. No.: 16/735,106

(22) Filed: Jan. 6, 2020

(65) Prior Publication Data
US 2020/0141915 A1 May 7, 2020

Related U.S. Application Data

(63) Continuation of application No. 15/520,708, filed as application No. PCT/US2014/062339 on Oct. 27, 2014, now Pat. No. 10,564,138.

(51) Int. Cl.
*G01N 33/00* (2006.01)
*F01N 3/20* (2006.01)
(Continued)

(52) U.S. Cl.
CPC ..... *G01N 33/0037* (2013.01); *B01D 53/9418* (2013.01); *B01D 53/9495* (2013.01);
(Continued)

(58) Field of Classification Search
CPC ........... G01N 33/0037; G01N 33/0004; G01N 27/02; Y02A 50/245; Y01T 10/24;
(Continued)

(56) References Cited

U.S. PATENT DOCUMENTS 7,217,355 B2 5/2007 Nair et al.
8,103,458 B2 1/2012 Wang et al.
(Continued)

FOREIGN PATENT DOCUMENTS

WO WO-2007/146369 A2 12/2007

OTHER PUBLICATIONS

International Search Report and Written Opinion issued for PCT Application No. PCT/US2014/062339, dated Feb. 10, 2015, 9 pages.

*Primary Examiner* — Robert R Raevis
(74) *Attorney, Agent, or Firm* — Foley & Lardner LLP

(57) ABSTRACT

An improved $NO_x$ sensor with an $NH_3$ oxidation. A sensor module may include a support component, a $NO_x$ sensing material positioned on the support component, and an $NH_3$ oxidation catalyst. The $NH_3$ oxidation catalyst may be layered on top of the $NO_x$ sensing material or the $NH_3$ oxidation catalyst may be positioned upstream of the $NO_x$ sensing material such that the $NH_3$ oxidation catalyst selectively converts $NH_3$ to $N_2$ while permitting $NO_x$ through to the $NO_x$ sensing material.

6 Claims, 3 Drawing Sheets

(51) Int. Cl.
    *C04B 35/48*    (2006.01)
    *B01J 37/02*    (2006.01)
    *B01J 37/00*    (2006.01)
    *B01D 53/94*    (2006.01)
    *F01N 13/00*    (2010.01)
    *F01N 3/10*    (2006.01)
    *G01N 27/02*    (2006.01)

(52) U.S. Cl.
    CPC ....... *B01J 37/0009* (2013.01); *B01J 37/0215* (2013.01); *C04B 35/48* (2013.01); *F01N 3/106* (2013.01); *F01N 3/2006* (2013.01); *F01N 3/2066* (2013.01); *F01N 13/008* (2013.01); *G01N 27/02* (2013.01); *C04B 2235/3225* (2013.01); *F01N 2510/00* (2013.01); *F01N 2510/06* (2013.01); *F01N 2560/026* (2013.01); *F01N 2570/18* (2013.01); *G01N 33/0004* (2013.01); *Y02A 50/245* (2018.01); *Y02T 10/24* (2013.01)

(58) Field of Classification Search
    CPC ........ F01N 3/2073; F01N 3/106; F01N 3/108; F01N 13/008; F01N 2510/06; F01N 2560/026; F01N 2570/18; F01N 3/2066; F01N 2510/00; C04B 35/48; C04B 2235/3225; B01J 37/0215; B01J 37/0009; B01D 53/9418; B01D 53/9495
    USPC ..................... 73/23.31, 114.71; 436/116–118
    See application file for complete search history.

(56) References Cited

U.S. PATENT DOCUMENTS

| | | |
|---|---|---|
| 8,141,347 B2 | 3/2012 | Kubinski et al. |
| 8,382,973 B2 | 2/2013 | Sugaya et al. |
| 2005/0056004 A1 | 3/2005 | Kakwani et al. |
| 2007/0125664 A1 | 6/2007 | Labarge et al. |
| 2011/0011152 A1 | 1/2011 | Ito et al. |
| 2011/0030343 A1 | 2/2011 | Kiser et al. |
| 2011/0030350 A1 | 2/2011 | Kato |
| 2013/0115152 A1* | 5/2013 | Nordberg ........... B01D 53/9431 423/212 |
| 2015/0165377 A1 | 6/2015 | Schroeder et al. |

\* cited by examiner

HIGHLY SELECTIVE NOX SENSOR IN THE PRESENCE OF NH3

CROSS-REFERENCE TO RELATED APPLICATIONS

The present application a continuation of U.S. patent application Ser. No. 15/520,708, filed Apr. 20, 2017, which is a National Phase Application of PCT/US2014/062339, filed Oct. 27, 2014. The contents of these applications are hereby incorporated by reference in their entireties.

TECHNICAL FIELD

The present application relates generally to the field of selective catalytic reduction (SCR) systems for an exhaust aftertreatment system.

BACKGROUND

For internal combustion engines, such as diesel engines, nitrogen oxide ($NO_x$) compounds may be emitted in the exhaust. To reduce $NO_x$ emissions, a SCR process may be implemented to convert the $NO_x$ compounds into more neutral compounds, such as diatomic nitrogen, water, or carbon dioxide, with the aid of a catalyst and a reductant. The catalyst may be included in a catalyst chamber of an exhaust system, such as that of a vehicle or power generation unit. A reductant, such as anhydrous ammonia, aqueous ammonia, or urea is typically introduced into the exhaust gas flow prior to the catalyst chamber. To introduce the reductant into the exhaust gas flow for the SCR process, an SCR system may dose or otherwise introduce the reductant through a dosing module that vaporizes or sprays the reductant into an exhaust pipe of the exhaust system up-stream of the catalyst chamber. The SCR system may include one or more sensors to monitor conditions within the exhaust system.

$NO_x$ sensors may have some cross sensitivity to $NH_3$ compounds, and this cross-sensitivity may cause errors in readings from the $NO_x$ sensors and, consequently, decrease SCR performance efficiency.

SUMMARY

Various embodiments relate to a $NO_x$ sensor that includes a support component, a $NO_x$ sensing material positioned on the support component, and an $NH_3$ oxidation catalyst proximate to the $NO_x$ sensing material. In some implementations, the $NH_3$ oxidation catalyst may be layered upon the $NO_x$ sensing material. The $NH_3$ oxidation catalyst may substantially cover the $NO_x$ sensing material. The support component may include a sample chamber of a sensor barrel. In some implementations, the $NH_3$ oxidation catalyst may coat a portion of an interior of the sample chamber of the sensor barrel. In some implementations, the $NO_x$ sensing material may include a ceramic type metal oxide. In particular embodiments, the $NO_x$ sensing material may include yttria-stabilized zirconia.

Other embodiments relate to a $NO_x$ sensor that includes a support component, a $NO_x$ sensing material positioned on the support component, and an $NH_3$ oxidation catalyst positioned upstream of the $NO_x$ sensing material. In some implementations, the $NH_3$ oxidation catalyst may be spaced apart from the $NO_x$ sensing material. The $NH_3$ oxidation catalyst may include an extruded catalyst. In other implementations, the $NH_3$ oxidation catalyst may include a coated substrate. The support component may include a sample chamber of a sensor barrel and the $NH_3$ oxidation catalyst may be affixed within the sample chamber of the sensor barrel and spaced apart from the $NO_x$ sensing material. In some implementations, the $NH_3$ oxidation catalyst may coat a portion of an interior of the sample chamber of the sensor barrel. The $NO_x$ sensing material may include a ceramic type metal oxide. Thee $NO_x$ sensing material may include yttria-stabilized zircons. The $NO_x$ sensor may further include a heating element configured to heat the $NH_3$ oxidation catalyst.

Further embodiments relate to a method of manufacturing a $NO_x$ sensor that includes providing a support component, applying a $NO_x$ sensing material to the support component, and applying a $NH_3$ oxidation catalyst to at least one of the support component or the $NO_x$ sensing material. In some implementations the $NH_3$ oxidation catalyst may include a layer of $NH_3$ oxidation catalyst applied to the $NO_x$ sensing material to substantially cover the $NO_x$ sensing material. The layer of $NH_3$ oxidation catalyst may be applied to a surface of the support component. The method of manufacturing the $NO_x$ sensor may further include coupling an electrode to the $NO_x$ sensing material.

BRIEF DESCRIPTION

The details of one or more implementations are set forth in the accompanying drawings and the description below. Other features, aspects, and advantages of the disclosure will become apparent from the description, the drawings, and the claims, in which:

Figure 1:
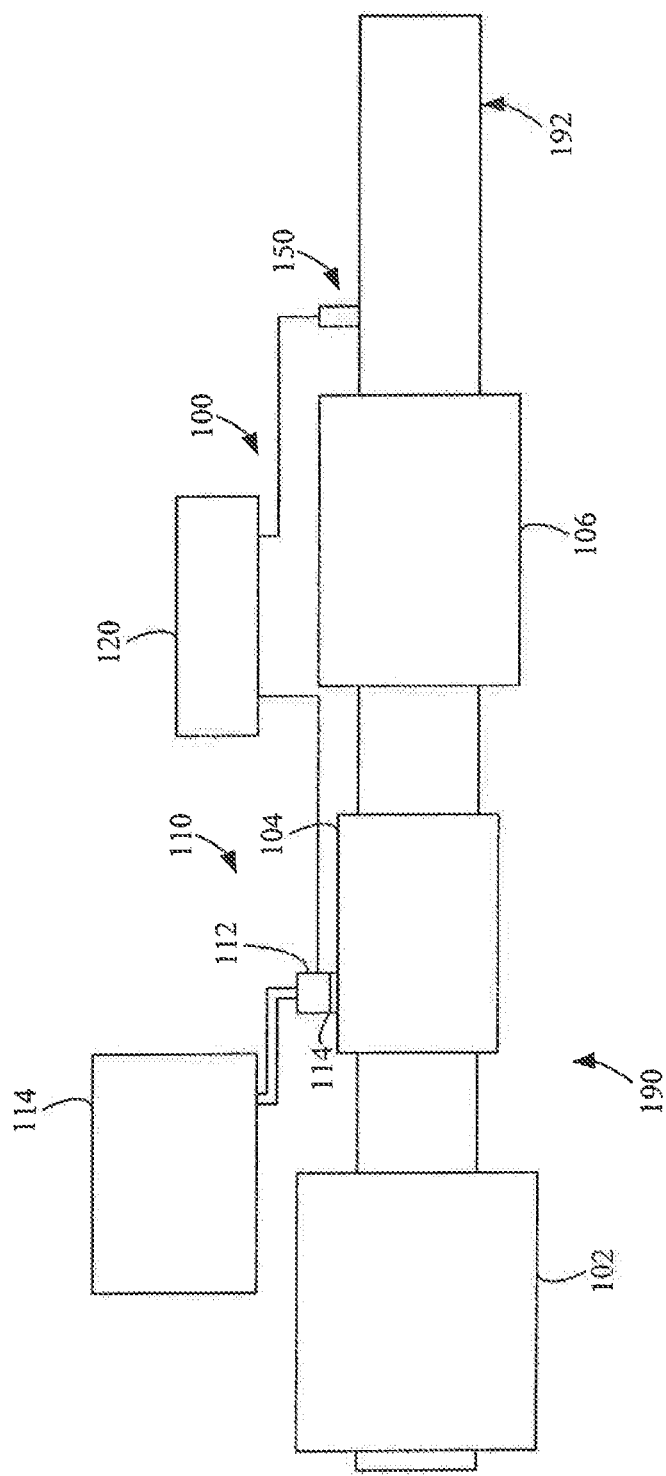
FIG. 1 is a block schematic diagram of an example selective catalytic reduction system having an example reductant delivery system for an exhaust system.

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

Following below are more detailed descriptions of various concepts related to, and implementations of, methods, apparatuses, and systems for reducing or eliminating $NH_3$ from a sample of exhaust gas for a $NO_x$ sensor. The various concepts introduced above and discussed in greater detail below may be implemented in any of numerous ways, as the described concepts are not limited to any particular manner of implementation. Examples of specific implementations and applications are provided primarily for illustrative purposes.

I. Overview

In some vehicles, $NO_x$ may be produced with other compounds as a result of combustion, such as for a diesel fuel vehicle, a diesel fuel power generator, etc. In some exhaust systems, a sensor module may be located upstream, downstream, or as part of an SCR catalyst to detect one or more emissions in the exhaust flow alter the SCR catalyst. For example, a $NO_x$ sensor, a CO sensor, and/or a particulate matter sensor may be positioned downstream of the SCR catalyst to detect $NO_x$, CO, and/or particulate matter within the exhaust gas exiting the exhaust of the vehicle. Such emission sensors may be useful to provide feedback to a controller to modify an operating parameter of the aftertreatment system of the vehicle. For example, a $NO_x$ sensor may be utilized to detect the amount of $NO_x$ exiting the vehicle exhaust system and, if the $NO_x$ detected is too high or too low, the controller may modify an amount of reductant delivered by a dosing module. A CO and/or a particulate matter sensor may also be utilized.

$NH_3$ compounds may be produced when urea or other $NH_3$ compounds are not reduced during the reduction of $NO_x$ via the SCR catalyst. In such instances, a sample reading by a $NO_x$ sensor may be offset based on the amount of $NH_3$ present in the exhaust sample for some $NO_x$ sensors. Various embodiments disclosed herein provide for a system to reduce or eliminate $NH_3$ compounds prior to a $NO_x$ sensing portion of a $NO_x$ sensor to reduce the error introduced by the $NH_3$ and/or to eliminate the need to separately determine the amount of $NH_3$ in the exhaust sample to correctly determine the $NO_x$ amount.

In some implementations, the $NH_3$ catalyst may be a separate component from the $NO_x$ sensor and positioned such that the $NH_3$ catalyst oxidizes $NH_3$ compounds in the exhaust stream sample to be delivered to the $NO_x$ sensor (e.g., as an ammonia filter or substrate element upstream of the $NO_x$ sensor in the exhaust stream, in an exhaust sample tube, and/or combinations thereof). In other implementations, the $NH_3$ catalyst may be a part of the $NO_3$ sensor, but may be positioned separate from the $NO_3$ sensing portion of the $NO_x$ sensor (e.g., as an ammonia filtering or substrate element within a sample chamber or tube of the $NO_x$ sensor, as a layer on a wall of a sample chamber or tube of the $NO_x$ sensor, and/or combinations thereof). In still further implementations, the $NH_3$ oxidation catalyst may be a part of the $NO_x$ sensor and may be positioned proximate to the $NO_x$ sensing portion of the $NO_x$ sensor (e.g., adjacent the $NO_3$ sensing portion, atop the $NO_x$ sensing portion, below the $NO_x$ sensing portion, and/or combinations thereof). Any of the foregoing implementations may be utilized to reduce or eliminate $NH_3$ compounds prior to a $NO_x$ sensing portion of a $NO_x$ sensor such that the detection of $NO_x$ within an exhaust sample may be improved. Such configurations may provide a more accurate $NO_x$ measurement for different zones of an aftertreatment or exhaust system. In addition, such configurations may also improve ammonia-to-$NO_x$ (ANR) control and improve SCR efficacy.

II. Overview of Aftertreatment System

FIG. 1 depicts an aftertreatment system 100 having an example reductant delivery system 110 for an exhaust system 190. The aftertreatment system 100 includes a diesel particulate filter (DPF) 102, the reductant delivery system 110, a decomposition chamber or reactor 104, a SCR catalyst 106, and a sensor probe 150.

The DPF 102 is configured to remove particulate matter, such as soot, from exhaust gas flowing in the exhaust system 190. The DPF 102 includes an inlet, where the exhaust gas is received, and an outlet, where the exhaust gas exits after having particulate matter substantially filtered from the exhaust gas and/or converting the particulate matter into carbon dioxide.

The decomposition chamber 104 is configured to convert a reductant, such as urea, aqueous ammonia, or diesel exhaust fluid (DEF), into ammonia. The decomposition chamber 104 includes a reductant delivery system 110 having a dosing module 112 configured to dose the reductant into the decomposition chamber 104. In some implementations, the urea, aqueous ammonia, DEF is injected upstream of the SCR catalyst 106. The reductant droplets then undergo the processes of evaporation, thermolysis, and hydrolysis to form gaseous ammonia within the exhaust system 190. The decomposition chamber 104 includes an inlet in fluid communication with the DPF 102 to receive the exhaust gas containing $NO_x$ emissions and an outlet for the exhaust gas, $NO_x$ emissions, ammonia, and/or remaining reductant to flow to the SCR catalyst 106.

The decomposition chamber 104 includes the dosing module 112 mounted to the decomposition chamber 104 such that the dosing module 112 may dose a reductant, such as urea, aqueous ammonia, or DEF, into the exhaust gases flowing in the exhaust system 190. The dosing module 112 may include an insulator 114 interposed between a portion of the dosing module 112 and the portion of the decomposition chamber 104 to which the dosing module 112 is mounted. The dosing module 112 is fluidly coupled to one or more reductant sources 116. In some implementations, a pump (not shown) may be used to pressurize the reductant source 116 for delivery to the dosing module 112.

The dosing module 112 is also electrically or communicatively coupled to a controller 120. The controller 120 is configured to control the dosing module 112 to dose reductant into the decomposition chamber 104. The controller 120 may include a microprocessor, an application-specific integrated circuit (ASIC), a field-programmable gate array (FPGA), etc., or combinations thereof. The controller 120 may include memory which may include, but is not limited to, electronic, optical, magnetic, or any other storage or transmission device capable of providing a processor, ASIC, FPGA, etc, with program instructions. The memory may include a memory chip, Electrically Erasable Programmable Read-Only Memory (EEPROM), erasable programmable read only memory (EPROM), flash memory, or any other suitable memory from which the controller 120 can read instructions. The instructions may include code from any suitable programming language.

The SCR catalyst 106 is configured to assist in the reduction of $NO_x$ emissions by accelerating a $NO_x$ reduction process between the ammonia and the $NO_x$ of the exhaust gas into diatomic nitrogen, water, and/or carbon dioxide. The SCR catalyst 106 includes inlet in fluid communication with the decomposition chamber 104 from which exhaust gas and reductant is received and an outlet in fluid communication with an end 192 of the exhaust system 190.

The exhaust system 190 may further include a diesel oxidation catalyst (DOC) in fluid communication with the exhaust system 190 (e.g., downstream of the SCR catalyst 106 or upstream of the DPF 102) to oxidize hydrocarbons and carbon monoxide in the exhaust gas.

The sensor probe 150 may be coupled to the exhaust system 190 to detect a condition of the exhaust gas flowing through the exhaust system 190. In some implementations, the sensor probe 150 may have a portion disposed within the exhaust system 190, such as a tip of the sensor probe 150 may extend into a portion or the exhaust system 190. In other implementations, the sensor probe 150 may receive exhaust gas through another conduit, such as a sample pipe extending from the exhaust system 190. While the sensor probe 150 is depicted as positioned downstream of the SCR catalyst 106, it should be understood that the sensor probe 150 may be positioned at any other position of the exhaust system 190, including upstream of the DPF 102, within the DPF 102, between the DPF 102 and the decomposition chamber 104, within the decomposition chamber 104, between the decomposition chamber 104 and the SCR catalyst 106, within the SCR catalyst 106, or downstream of the SCR catalyst 106. In addition, two or more sensor probes 150 may be utilized for detecting a condition of the exhaust gas, such as two, three, four, five, or size sensor probes 150 with each sensor probe 150 located at one of the foregoing positions of the exhaust system 190. In some implementations a first sensor probe 150 may be upstream of the SCR catalyst 106 and a second sensor probe 150 may be downstream of the SCR catalyst 106. In other implementations, the first sensor probe 150 may be upstream of the decomposition chamber 104 and the second sensor probe 150 may be downstream of the SCR catalyst 106. In still other implementations, the first sensor probe 150 may be upstream of the DPF 102, and the sensor probe 150 may be downstream of the SCR catalyst 106. Still further configurations for the sensor probes 150 may be implemented.

III. Implementations of $NO_x$ Sensors

Figure 2:
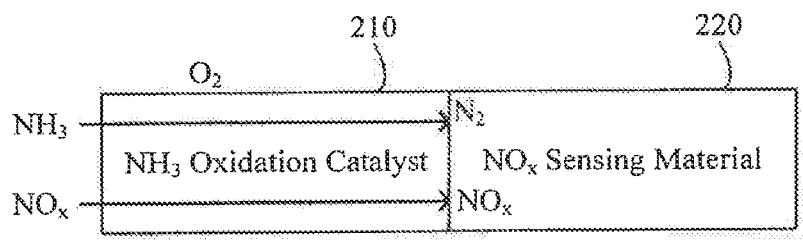
FIG. 2 is a block diagram showing a $NO_x$ sensing material and a $NH_3$ catalyst material showing the oxidation of $NH_3$ to $N_2$ and $O_2$.

FIG. 2 depicts a block diagram of an example $NH_3$ oxidation catalyst 210 and a $NO_x$ sensor sensing material 220. The $NH_3$ oxidation catalyst 210 may be an extruded, coated, powder or any other form of $NH_3$ oxidation catalyst 210 that can be positioned before the $NO_x$ sensor sensing material 220. For instance, the $NH_3$ oxidation catalyst 210 may be installed before the $NO_x$ sensor sensing material 220 of a $NO_x$ sensor. The $NH_3$ oxidation catalyst 210 may be a separate catalyst than the DOC. That is, the $NH_3$ oxidation catalyst 210 may be a separate catalyst within a housing of the $NO_x$ sensor. In other implementations, the $NH_3$ oxidation catalyst 210 may be separate from than $NO_x$ sensor or may be one part of a package with a $NO_x$ sensor. In further implementations, the $NH_3$ oxidation catalyst 210 may comprise a layer of catalyst atop the $NO_x$ sensor sensing material 220. The $NO_x$ sensor sensing material 220 may be ceramic type metal oxide, such as yttria-stabilized zirconia (YSZ) or any other suitable $NO_x$ sensor sensing material 220. The $NH_3$ oxidation catalyst 210 may be designed to have high selectivity to $N_2$ based on the type of catalyst used, such as precious metal or mixed oxide. For example, the $NH_3$ oxidation catalyst 210 may be a catalyst having one or more of the following compositions: $LaNiO_3$, $La_{0.75}Sr_{0.21}MnO_3$, MeO/support Me=Co, Fe, Cr, Mn, Bi, $\alpha$-$Fe_2O_3$, mixed oxides of V. Be, Ba, Cu, $\alpha$-$Fe_2O_3$ $Cr_2O_3$, $\alpha$-$Fe_2O_3$+$ZrO_2$, $Co_3O_4$+alumina (5-45%), thoria, ceria, zinc, and calcium oxides pellets or extrudates, $Co_3O_4$+0.1-10% $Li_2O$ pellets, grains, monoliths), $Co_3O_4$ or $Bi_2O_3$ promoted by rare earth element or thorium (and may also contain at least one of oxides of Mn, Fe, Mg, Cr or Nb), $\alpha$-$Fe_2O_3$—$MAl_2O_4$—$Bi_2O_3$—$Ce_2O_3$ (where M=Mg, Mn, Ca, Sr, Ba), precious metal based catalysts (e.g., using Pt, Pd, Rh, and/or Ir) or other suitable $NH_3$ oxidation catalysts. In some implementations, the $NH_3$ oxidation catalyst 210 may be selected based, at least in part, on an operating temperature for the $NO_x$ sensor.

As shown in FIG. 2, the $NH_3$ oxidation catalyst 210 selectively converts $NH_3$ to $N_2$ while substantially permitting $NO_x$ to pass through to the $NO_x$ sensor sensing material 220. In some implementations, the $NH_3$ oxidation catalyst 210 may have separate heating element for the $NH_3$ oxidation catalyst 210 to operate at a temperature that is different than the temperature for the $NO_x$ sensor sensing material 220. For example, an electric heating element or combustion heating element may raise the temperature of the exhaust gas and/or the $NH_3$ oxidation catalyst 210 to a predetermined temperature for the $NH_3$ oxidation catalyst 210 to operate at to selectively convert $NH_3$. In other implementations, the operating temperature for the $NH_3$ oxidation catalyst 210 may be substantially the same as that of the $NO_x$ sensor sensing material 220.

Figure 3:
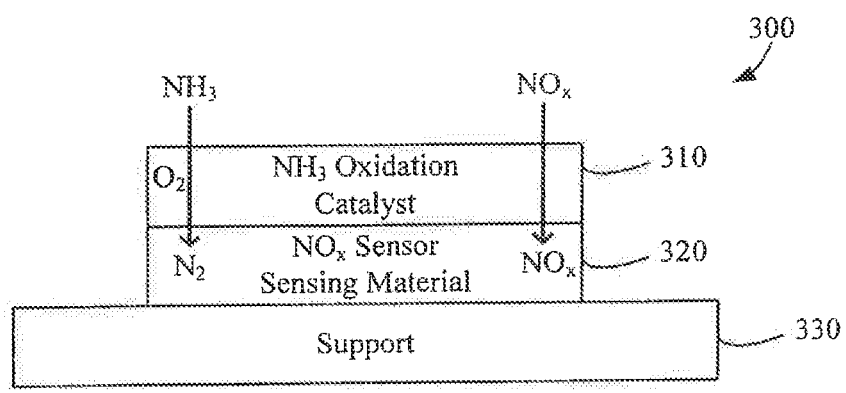
FIG. 3 is a block diagram of an example $NO_x$ sensor having a $NH_3$ catalyst positioned proximate a $NO_x$ sensing material.

FIG. 3 depicts an example block schematic configuration for a $NO_x$ sensor 300. The $NO_x$ sensor 300 may include a $NH_3$ oxidation catalyst 310, a $NO_x$ sensor sensing material 320, and a support component 330. The support component 330 may be any suitable component, such as a sensor body, upon which the $NO_x$ sensor sensing material 320 may be positioned and used for the $NO_x$ sensor 300. In some implementations, the support component 330 may be a metallic member, such as a metal plate, a metallic sensor barrel, etc. In other implementations, the support member 330 may be a composite material, a ceramic material, etc. The $NO_x$ sensor sensing material 320 may be ceramic type metal oxide, such as yttria-stabilized zirconia (YSZ) or any other suitable $NO_x$ sensing material. The $NH_3$ oxidation catalyst 310 may be a catalyst having one or more of the following compositions: $LaNiO_3$, $La_{0.75}Sr_{0.21}MnO_3$, MeO/support Me=Co, Fe, Cr, Mn, Bi, $\alpha$-$Fe_2O_3$, mixed oxides of Y, Be, Ba, Cu, $\alpha$-$Fe_2O_3$ $Cr_2O_3$, $\alpha$-$Fe_2O_3$+$ZrO_2$, $Co_3O_4$+alumina (5-15%), thoria, ceria, zinc, and calcium oxides pellets or extrudates, $Co_3O_4$+0.1-10% $Li_2O$ pellets, grains, monoliths), $Co_3O_4$ or $Bi_2O_3$ promoted by rare earth element or thorium (and may also contain at least one of oxides of Mn, Fe, Mg, Cr or Nb), $\alpha$-$Fe_2O_3$$MAl_2O_4$—$Bi_2O_3$—$Ce_2O_3$ (where M=Mg, Mn, Ca, Sr, Ba), precious metal based catalysts (e.g., using Pt, Pd, Rh, and/or Ir) or other suitable $NH_3$ oxidation catalysts. In some implementations, the $NH_3$ oxidation catalyst 310 may be selected based, at least in part, on an operating temperature for the $NO_x$ sensor 300.

In the implementation shown in FIG. 3, the $NH_3$ oxidation catalyst 310 is positioned proximate (e.g., near to) the $NO_x$ sensor sensing material 320 such that the $NH_3$ oxidation catalyst 310 selectively converts $NH_3$ to $N_2$ while substantially permitting $NO_x$ to pass through to the $NO_x$ sensor sensing material 320. The $NH_3$ oxidation catalyst 310 may be a separate catalyst than the DOC. That is, the $NH_3$ oxidation catalyst 310 may be a separate catalyst within a housing of the $NO_x$ sensor 300. In some implementations, the $NH_3$ oxidation catalyst 310 may be layered atop the $NO_x$ sensor sensing material 320. For instance, the $NO_x$ sensor sensing material 320 may be layered on a support component 330 of the $NO_x$ sensor 300, such as a layer of YSZ within a sample chamber (e.g., a metallic barrel) of the $NO_x$ sensor 300. In some implementations, the $NO_x$ sensor sensing material 320 may substantially cover an entire surface of the support component 330 (e.g., as a layer on the interior end of a sample chamber of a $NO_x$ sensor). Suitable electrodes (e.g., gold, platinum, palladium, etc.) for the $NO_x$ sensor 300 may be positioned relative to the $NO_x$ sensor sensing material 320 (e.g., attached, coupled, integrated into, or otherwise connected) such that the electrodes may detect a change in voltage across the $NO_x$ sensor sensing material 320 based on the interaction of $NO_x$ in an exhaust sample interacting with the $NO_x$ sensor sensing material 320.

A layer of $NH_3$ oxidation catalyst 310 may substantially cover the $NO_x$ sensor sensing material 320 such that the exhaust gas sample must pass through the $NH_3$ oxidation catalyst 310 before encountering the $NO_x$ sensor sensing material 320. Thus, $NH_3$ within the exhaust gas sample may substantially be oxidized by the $NH_3$ oxidation catalyst 310 prior to encountering the $NO_x$ sensor sensing material 320. Thus, the amount of $NH_3$ that may affect the detection of $NO_x$ within the exhaust gas sample may be substantially reduced, thereby improving the $NO_x$ detection of the $NO_x$ sensor 300. In some implementations, the $NH_3$ oxidation catalyst 310 may be layered on the top and sides of a support component 330 and/or the $NO_x$ sensor sensing material 320. In further implementations, the $NH_3$ oxidation catalyst 310 may be a layer coating the part or the entire interior of a sample chamber of the $NO_x$ sensor 300 in addition to or in lieu of a layer on the $NO_x$ sensor sensing material 320. In some implementations, the $NH_3$ oxidation catalyst 310 may also coat part or all of the exterior surfaces of a sample probe portion of the $NO_x$ sensor 300.

In some implementations, the $NH_3$ oxidation catalyst 310 may be an extruded oxidation catalyst, a coating or layer of oxidation catalyst, a powdered oxidation catalyst, and/or other configuration for the $NH_3$ oxidation catalyst 310.

Figure 4:
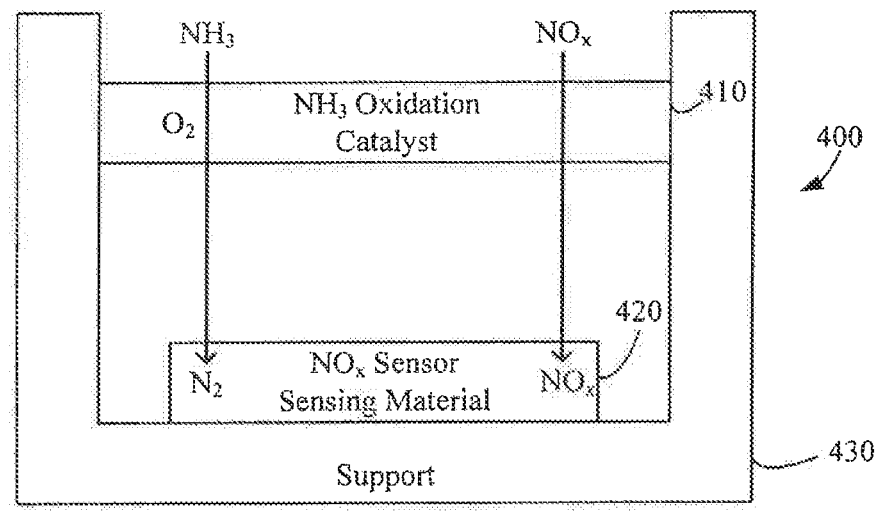
FIG. 4 is a block diagram of another example $NO_x$ sensor having a $NH_3$ catalyst positioned upstream of a $NO_x$ sensing material.

FIG. 4 depicts another example block schematic configuration for a $NO_x$ sensor 400 having a $NH_3$ oxidation catalyst 410 positioned upstream of a $NO_x$ sensor sensing material 420. In the example depicted in FIG. 4, the $NH_3$ oxidation catalyst 410 is supported by the support component 430 of the $NO_x$ sensor 400, but it should be understood that the $NH_3$ oxidation catalyst 410 described herein may be separate from the $NO_x$ sensor 400 (e.g., as a separate component positioned upstream in an exhaust system, as a component attached to a sensor probe portion of the $NO_x$ sensor 400, etc.). The support component 430 of $NO_x$ sensor 400 may be any suitable component upon which the $NO_x$ sensor sensing material 420 may be positioned and used for the $NO_x$ sensor 400. In some implementations the support component 430 may be a metallic member, such as a metal plate, a metallic sensor barrel, etc. In other implementations, the support member 430 may be a composite material, a ceramic material, etc. The $NO_x$ sensor sensing material 420 may be ceramic type metal oxide, such as yttria-stabilized zirconia (YSZ) or any other suitable $NO_x$ sensing material. The $NH_3$ oxidation catalyst 410 may be a catalyst having one or more of the following compositions: $LaNiO_3$, $La_{0.75}Sr_{0.21}MnO_3$, MeO/support Me=Co, Fe, Cr, Mn, Bi, $\alpha$-$Fe_2O_3$, mixed oxides of Y, Be, Ba, Cu, $\alpha$-$Fe_2O_3$ $Cr_2O_3$, $\alpha$-$Fe_2O_3$ $Cr_2O_3$, $\alpha Fe_2O_3$+$ZrO_2$, $Co_3O_4$+alumina (5-15%), thoria, ceria, zinc, and calcium oxides pellets or extrudates, $Co_3O_4$+0.1-10% $Li_2O$ pellets, grains, monoliths), $Co_3O_4$ or $Bi_2O_3$ promoted by rare earth element or thorium (and may also contain at least one of oxides of Mn, Fe, Mg, Cr or Nb), $\alpha$-$Fe_2O_3$—$MAl_2O_4$—$Bi_2O_3$—$Ce_2O_3$ (where M=Mg, Mn, Ca, Sr, Ba), precious metal based catalysts (e.g., using Pt, Pd, Rh, and/or Ir) or other suitable $NH_3$ oxidation catalysts. In some implementations, the $NH_3$ oxidation catalyst 410 may be selected based, at least in part, on an operating temperature for the $NO_x$ sensor 400.

In the implementation shown in FIG. 4, the $NH_3$ oxidation catalyst 410 is positioned upstream of the $NO_x$ sensor sensing material 420 such that the $NH_3$ oxidation catalyst 410 selectively converts $NH_3$ to $N_2$ while substantially permitting $NO_x$ to pass through to the $NO_x$ sensor sensing material 420. In some implementations, the $NH_3$ oxidation catalyst 410 may be coated on a support structure, such as a filter or substrate body or a portion of the support component 430, upstream of the $NO_x$ sensor sensing material 420. The $NH_3$ oxidation catalyst 410 may be a separate catalyst than the DOC. That is, the $NH_3$ oxidation catalyst 410 may be a separate catalyst within a housing of the $NO_x$ sensor 400. For instance, the $NO_x$ sensor sensing material 420 may be layered on a portion of the support component 430 of the $NO_x$ sensor 400, such as a layer of YSZ, within a sample chamber (e.g., a metallic barrel) of the $NO_x$ sensor 400. In some implementations, the $NO_x$ sensor sensing material 420 may substantially cover an entire surface of the support component 430 (e.g., as a layer on the interior end of a sample chamber of a $NO_x$ sensor). Suitable electrodes (e.g., gold, platinum, palladium, etc.) for the $NO_x$ sensor 400 may be positioned relative to the $NO_x$ sensor sensing material 420 (e.g., attached, coupled, integrated into, or otherwise connected) such that the electrodes may detect a change in voltage across the $NO_x$ sensor sensing material 420 based on the interaction of $NO_x$ in an exhaust sample interacting with the $NO_x$ sensor sensing material 420.

In some implementations, the $NH_3$ oxidation catalyst 410 may be applied to a portion of the support component 430 or a separate component upstream of the layer of $NO_x$ sensor sensing material 420. For example, the $NH_3$ oxidation catalyst 410 may be an extruded filter/substrate or coated filter/substrate that may be positioned upstream of the $NO_x$ sensor sensing material 420. In some implementations, the $NH_3$ oxidation catalyst 410 may be affixed to the support component 430 of the $NO_x$ sensor 400. Thus, the $NH_3$ oxidation catalyst 410 may be spaced apart from the $NO_x$ sensor sensing material 420 of the $NO_x$ sensor 400. In some implementations, a heating element may be provided to heat the $NH_3$ oxidation catalyst 410 and/or the exhaust gas sample encountering the $NH_3$ oxidation catalyst 410 such that the $NH_3$ oxidation catalyst 410 and/or the exhaust gas sample operates at a temperature that is different than the temperature for the $NO_x$ sensor sensing material 420. For example, an electric heating element or combustion heating element may raise the temperature of the exhaust gas sample and/or the $NH_3$ oxidation catalyst 410 to a predetermined temperature for the $NH_3$ oxidation catalyst 410 to operate at to selectively convert $NH_3$. In an implementation, a portion of a sample chamber housing the $NH_3$ oxidation catalyst 410 may be insulated relative to a portion of the sample chamber housing the $NO_x$ sensor sensing material 420. Thus, the portion of the sample chamber housing the $NH_3$ oxidation catalyst 410 may be heated (e.g., via resistive/electrical heating and/or combustion heating) for the $NH_3$ oxidation catalyst 410 to operate at a first temperature while the insulation insulates the portion of the sample chamber housing the $NO_x$ sensor sensing material 420 to operate at a second temperature different from the first temperature.

In some other implementations, the $NH_3$ oxidation catalyst 410 may be a powdered $NH_3$ oxidation catalyst 410 that may be filled into a sample chamber of the $NO_x$ sensor 400 with a membrane to contain the $NH_3$ oxidation catalyst 410 within the sample chamber while permitting the exhaust gas sample containing $NH_3$ and/or $NO_x$ to pass through to the $NO_x$ sensor sensing material 420.

In any of the foregoing describe implementations and/or combinations thereof, the $NH_3$ oxidation catalyst 410 may also coat part or the entire interior of a sample chamber of the $NO_x$ sensor 400. In any of the foregoing describe implementations and/or combinations thereof, the $NH_3$ oxidation catalyst 410 may also coat part or all of the exterior surfaces of a sample probe portion of the $NO_x$ sensor 400.

Figure 5:
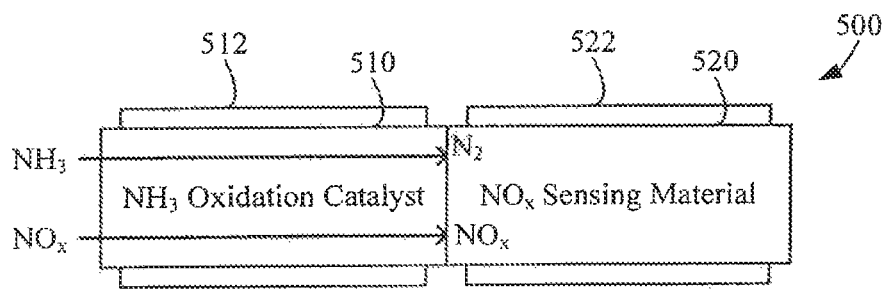
FIG. 5 is a block diagram of another example $NO_x$ sensor having a $NH_3$ catalyst positioned upstream of a $NO_x$ sensing material and having independent heating elements.

FIG. 5 is a block diagram of an example $NH_3$ oxidation catalyst 510 and a $NO_x$ sensor sensing material 520 for yet another $NO_x$ sensor 500. The $NH_3$ oxidation catalyst 510 may be an extruded, coated, powder or any other form of $NH_3$, oxidation catalyst 510 that can be positioned before the $NO_x$ sensor sensing material 520. For instance, the $NH_3$ oxidation catalyst 510 may be installed before the $NO_x$ sensor sensing material 520 of a $NO_x$ sensor. In other implementations, the $NH_3$ oxidation catalyst 510 may be separate from than $NO_x$ sensor 500 or may be one part of a package with a $NO_x$ sensor 500. In further implementations, the $NH_3$ oxidation catalyst 510 may comprise a layer of catalyst atop the $NO_x$ sensor sensing material 520. The $NO_x$ sensor sensing material 520 may be ceramic type metal oxide, such as yttria-stabilized zirconia (YSZ) or any other suitable $NO_x$ sensing material. The $NH_3$ oxidation catalyst 510 may be designed to have high selectivity to $N_2$ based on the type of catalyst used, such as precious metal or mixed oxide. For example, the $NH_3$ oxidation catalyst 510 may be a catalyst having one or more of the following compositions: $LaNiO_3$, $La_{0.75}Sr_{0.21}MnO_3$, MeO/support Me=Co, Fe, Cr, Mn, Bi, $\alpha$-$Fe_2O_3$, mixed oxides of Y, Be, Ba, Cu, $\alpha$-$Fe_2O_3$ $Cr_2O_3$, $\alpha$-$Fe_2O_3$+$ZrO_2$, $Co_3O_4$+alumina (5-15%), thoria, coria, zinc, and calcium oxides pellets or extrudates, $Co_3O_4$+ 0.1-10% $Li_2O$ pellets, grains, monoliths), $Co_3O_4$ or $Bi_2O_3$ promoted by rare earth element or thorium (and may also contain at least one of oxides of Mn, Fe, Mg, Cr or Nb), $\alpha$-$Fe_2O_3$—$MAl_2O_4$—$Bi_2O_3$—$Ce_2O_3$ (where M=Mg, Mn, Ca, Sr, Ba), precious metal based catalysts (e.g., using Pt, Pd, Rh, and/or H) or other suitable $NH_3$ oxidation catalysts. In some implementations, the $NH_3$ oxidation catalyst 510 may be selected based, at least in part, on an operating temperature for the $NO_x$ sensor 500.

As shown in FIG. 5, the $NH_3$ oxidation catalyst 510 selectively converts $NH_3$ to $N_2$ while substantially permitting $NO_x$ to pass through to the $NO_x$ sensor sensing material 520. The $NH_3$ oxidation catalyst 510 may be a separate catalyst than the DOC. That is, the $NH_3$ oxidation catalyst 510 may be a separate catalyst within a housing of the $NO_x$ sensor 500. In some implementations, the $NH_3$ oxidation catalyst 510 may have first heating and/or cooling element 512 for the $NH_3$ oxidation catalyst 510 to operate at a first temperature that is different than a second temperature for the $NO_x$ sensor sensing material 520. For example, an electric heating and/or cooling element or combustion heating and/or cooling element 512 may raise or lower the temperature of the exhaust gas and/or the $NH_3$ oxidation catalyst 510 to a predetermined first temperature for the $NH_3$ oxidation catalyst 510 to operate at to selectively convert $NH_3$.

In some implementations, the $NO_x$ sensor sensing material 520 may have second heating and/or cooling element 522 for the $NO_x$ sensor sensing material 520 to operate at a second temperature that is different than the first temperature for the $NH_3$ oxidation catalyst 510. For example, an electric heating and/or cooling element or combustion heating and/or cooling element 522 may raise the temperature of the exhaust gas and/or the $NO_x$ sensor sensing material 520 to a predetermined second temperature for the $NO_x$ sensor sensing material 520 to operate at to selectively convert $NO_x$. In other implementations, the first temperature for the $NH_3$ oxidation catalyst 510 may be substantially the same as the second temperature for the $NO_x$ sensor sensing material 520.

Any of the foregoing $NO_x$ sensors 300, 400, 500 may be coupled to a portion of an exhaust system, such as exhaust system 190 of FIG. 1, such that the $NO_x$ content within the exhaust gas may be sampled and measured, such as upstream of the DPF 102, within the DPF 102, between the DPF 102 and the decomposition chamber 104, within the decomposition chamber 104, between the decomposition chamber 104 and the SCR catalyst 106, within the SCR catalyst 106, downstream of the SCR catalyst 106, or any other portion of the exhaust system 190. In some implementations, several $NO_x$ sensors 300, 400, 500 may be used at any combination of the foregoing portions of the exhaust system 190.

The term "controller" encompasses all kinds of apparatus, devices, and machines for processing data, including by way of example a programmable processor, a computer, a system on a chip, or multiple ones, a portion of a programmed processor, or combinations of the foregoing. The apparatus can include special purpose logic circuitry, e.g., an FPGA or an ASIC. The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as distributed computing and grid computing infrastructures.

A computer program (also known as a program, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code).

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

As utilized herein, the term "substantially" and any similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided unless otherwise noted. Accordingly, these terms should be interpreted as indicating that insubstantial or inconsequential modifications or alterations of the subject matter described and claimed are considered to be within the scope of the invention as recited in the appended claims. Additionally, it is noted that limitations in the claims should not be interpreted as constituting "means plus function" limitations under the United States patent laws in the event that the term "means" is not used therein.

The terms "coupled," "connected," and the like as used herein mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another or with the two components or the two components and any additional intermediate components being attached to one another.

The terms "fluidly coupled," "in fluid communication," and the like as used herein mean the two components or objects have a pathway formed between the two components or objects in which a fluid, such as water, air, gaseous reductant, gaseous ammonia, etc., may flow, either with or without intervening components or objects. Examples of fluid couplings or configurations for enabling fluid communication may include piping, channels, or any other suitable components for enabling the flow of a fluid from one component or object to another.

It is important to note that the construction and arrangement of the system shown in the various exemplary implementations is illustrative only and not restrictive in character. All changes and modifications that come within the spirit and/or scope of the described implementations are desired to be protected. It should be understood that some features may not be necessary and implementations lacking the various features may be contemplated as within the scope of the application, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A NOx sensor comprising:
    a NOx sensing material;
    an NH3 oxidation catalyst coupled to the NOx sensing material and located upstream of the NOx sensing material; and
    a temperature control element operatively coupled to the NH3 oxidation catalyst and configured to heat or cool the NH3 oxidation catalyst so as to control an operating temperature of the NH3 oxidation catalyst.

2. The NOx sensor of claim 1, wherein the temperature control element is configured to cause the NH3 oxidation catalyst to operate at a first temperature that is different from a second temperature of the NOx sensing material.

3. The NOx sensor of claim 1, wherein the temperature control element is configured to cause the NH3 oxidation catalyst to operate at a first temperature that is the same as a second temperature of the NOx sensing material.

4. The NOx sensor of claim 1, wherein:
    the temperature control element is a first temperature control element, and
    the NOx sensor further comprises a second temperature control element operatively coupled to the NOx sensing material and configured to heat or cool the NOx sensing material so as to control an operating temperature of the NOx sensing material.

5. The NOx sensor of claim 1, wherein the NH3 oxidation catalyst comprises an extruded catalyst.

6. The NOx sensor of claim 1, wherein the NH3 oxidation catalyst comprises a coated substrate.

* * * * *